(12) United States Patent
Harbers

(10) Patent No.: US 7,520,978 B2
(45) Date of Patent: Apr. 21, 2009

(54) FLUID PURIFICATION SYSTEM WITH ULTRA VIOLET LIGHT EMITTERS

(75) Inventor: Gerard Harbers, Sunnyvale, CA (US)

(73) Assignee: Philips Lumileds Lighting Co., LLC, San Jose, CA (US)

( * ) Notice: Subject to any disclaimer, the term of this patent is extended or adjusted under 35 U.S.C. 154(b) by 673 days.

(21) Appl. No.: 11/156,102

(22) Filed: Jun. 17, 2005

(65) Prior Publication Data
US 2006/0283786 A1   Dec. 21, 2006

(51) Int. Cl.
*A61L 2/10* (2006.01)

(52) U.S. Cl. .............................. 210/143; 96/16; 96/418; 96/422; 210/87; 210/94; 210/97; 210/192; 250/435; 250/438; 422/111; 422/186.3; 361/761; 361/806

(58) Field of Classification Search .................. 210/85, 210/87, 103, 143, 192, 193, 739, 748, 97; 210/149, 94; 250/435–438, 455.1, 504 R; 422/24, 105–111, 186.3; 204/158.2; 73/861.47; 96/16, 224, 417, 420, 422, 418; 361/748, 361/761, 806, 807; 174/250

See application file for complete search history.

(56) References Cited

U.S. PATENT DOCUMENTS

| | | | | |
|---|---|---|---|---|
| 4,400,270 A | * | 8/1983 | Hillman | 210/103 |
| 4,555,717 A | * | 11/1985 | Miura et al. | 347/21 |
| 5,368,826 A | * | 11/1994 | Weltz et al. | 422/243 |
| 5,471,063 A | * | 11/1995 | Hayes et al. | 250/436 |
| 5,671,678 A | * | 9/1997 | Bolte et al. | 101/491 |
| 5,780,748 A | * | 7/1998 | Barth | 73/861.47 |
| 6,524,447 B1 | * | 2/2003 | Carmignani et al. | 204/158.2 |
| 7,137,696 B2 | * | 11/2006 | Siegel | 347/102 |
| 7,169,311 B2 | * | 1/2007 | Saccomanno | 210/748 |
| 7,393,095 B2 | * | 7/2008 | Oshima et al. | 347/102 |
| 2004/0101291 A1 | * | 5/2004 | Takabayashi et al. | 386/125 |
| 2006/0131246 A1 | * | 6/2006 | Ehlers | 210/748 |
| 2008/0094841 A1 | * | 4/2008 | Dahm | 362/294 |

* cited by examiner

*Primary Examiner*—Joseph W Drodge
(74) *Attorney, Agent, or Firm*—Patent Law Group; Rachel Leiterman

(57) ABSTRACT

A system for purifying a fluid uses ultra violet (UV) light to inactivate micro-organisms present in the fluid. The system has an arrangement of UV light emitters on perforated plates. The fluid, while passing through perforations in the perforated plates, is exposed to the UV light emitted by the UV light emitters. Micro-organisms present in the fluid pass very close to the UV light emitters. The UV light absorbed by the micro-organisms causes genetic damage and inactivation. The system has feedback units providing feedback about the physical properties of the fluid to a power unit supplying power to the UV light emitters. The power unit varies the amount of power supplied to the UV light emitters, based on the feedback.

16 Claims, 5 Drawing Sheets

FLUID PURIFICATION SYSTEM WITH ULTRA VIOLET LIGHT EMITTERS

FIELD OF INVENTION

This invention relates to a system for purification of fluids using Ultra Violet (UV) light, and in particular, to a system for purification of fluids using UV light emitters mounted on perforated plates.

BACKGROUND

Some fluids like water and air, used in day-to-day life, can be contaminated with micro-organisms. The presence of micro-organisms in fluids, for example, in water used for drinking, may have a detrimental effect on the health of the consumer. Hence, the micro-organisms present in fluids should be inactivated before the fluids are used for consumption.

One way of purifying fluids is by using ultra violet (UV) light emitted by an UV light emitter. UV light, in the range of 260-to-280 nm, is absorbed by the DNA, RNA and protein in micro-organisms, for example bacteria and virus, causing genetic damage and inactivation.

There exist systems which use UV light for the purification of fluids. However, the known systems for purification of fluids using the UV light require a good transmittance of the fluids. Transmittance, in terms of fluid treatment with UV light, is the ability of the UV light to travel through a fluid, or more specifically, the fraction of a given amount of the UV light that can be measured through the fluid at a given point. Currently, commercially available UV fluid purification systems require that at least 75% of transmitted UV light reaches a distance of 1 cm from the UV light emitters. As the turbidity of the fluids increases, their transmittance decreases. Low transmittance of the fluids decreases the amount of exposure of the micro-organisms to UV light, thereby, reducing the effectiveness of the known systems in inactivating these micro-organisms.

What is needed is a system for the purification of fluids that can work efficiently even for a fluid with a low transmittance.

SUMMARY

The present invention provides a system that is used for the purification of fluids, using UV light emitters mounted on perforated plates.

In one embodiment, perforated plates with UV light emitters mounted on them are housed inside a chamber. A fluid that is to be purified passes through perforations in the perforated plates. The UV light emitters are mounted very close to the perforations. The dimensions of the perforations in the perforated plates are such that micro-organisms present in the fluid come in close proximity to the UV light emitted by the UV light emitters. In case of high turbidity of the fluid, which results in low transmittance of the UV light, the close exposure of the micro-organisms to the UV light emitters ensures that the micro-organisms absorb a sufficient amount of UV light required for their inactivation.

In another embodiment, the invention also employs a feedback-based power control unit and feedback units to control power supplied to the UV light emitters. The feedback units provide data about the physical properties of the fluid to the feedback-based power control unit. Based on the received data, for example flow-rate of the fluid and intensity of the UV light inside the fluid, the feedback-based power control unit varies the amount of power supplied to the UV light emitters.

In yet another embodiment, the invention employs UV light-reflecting screens on walls of the chamber, to increase density of the UV light inside it.

BRIEF DESCRIPTION OF THE DRAWINGS

Elements in the various figures designated by the same numerals may be similar or identical to one other.

DETAILED DESCRIPTION

Figure 1:
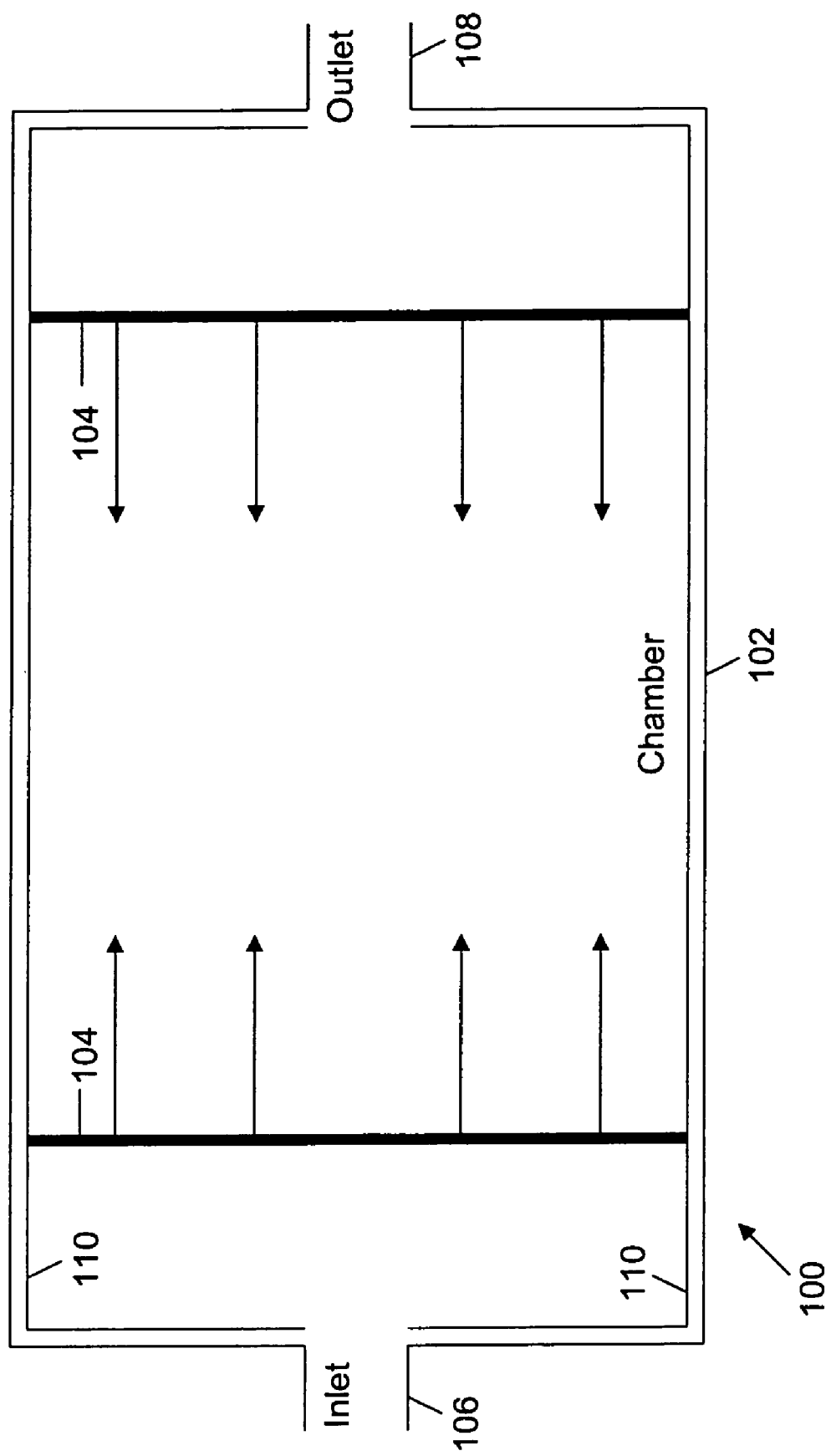
FIG. 1 is a diagram depicting a system for the purification of a fluid, in accordance with an embodiment of the invention.

FIG. 1 is a diagram depicting a system 100 for the purification of a fluid, in accordance with an embodiment of the invention. Two perforated plates 104 are housed inside chamber 102. Perforated plates 104 have UV light emitters mounted on their surface. In an embodiment of the invention, perforated plates 104 may be modified to fit into any other container. For example, perforated plates 104 may be modified to fit into a cylindrical pipe carrying water. Chamber 102 has an inlet 106 and an outlet 108. The fluid enters chamber 102 through inlet 106 and passes through perforations in perforated plates 104. The fluid may be air, water or any other liquid or gas. The UV light emitters may be UV Light Emitting Diodes (LEDs), such as UVTOP LEDs, manufactured by Sensor Electronic Technology Inc.

The micro-organisms present in the fluid, while passing through the perforations in perforated plates 104, are exposed to UV light emitted by the UV light emitters. The UV light is absorbed by the DNA, RNA and protein in the micro-organisms. The UV light causes genetic disorder and inactivation of the micro-organisms. Perforated plates 104 expose both front and rear of the micro-organisms to the UV light.

In an embodiment of the invention, a feedback-based power control unit and feedback units are employed to control amount of power supplied to the UV light emitters (This is not shown in FIG. 1). The feedback units provide data about the physical properties of the fluid to the feedback-based power control unit. Depending on the received data, the feedback-based power control unit varies the amount of power supplied to the UV light emitters.

System 100 also includes UV-reflecting screens 110. UV-reflecting screens 110 cover walls of chamber 102. Any UV light incident on UV reflecting screens 110 is reflected back to chamber 102, increasing density of the UV light inside chamber 102. In an embodiment of the invention, UV-reflecting screens 110 are made of aluminium.

Figure 2:
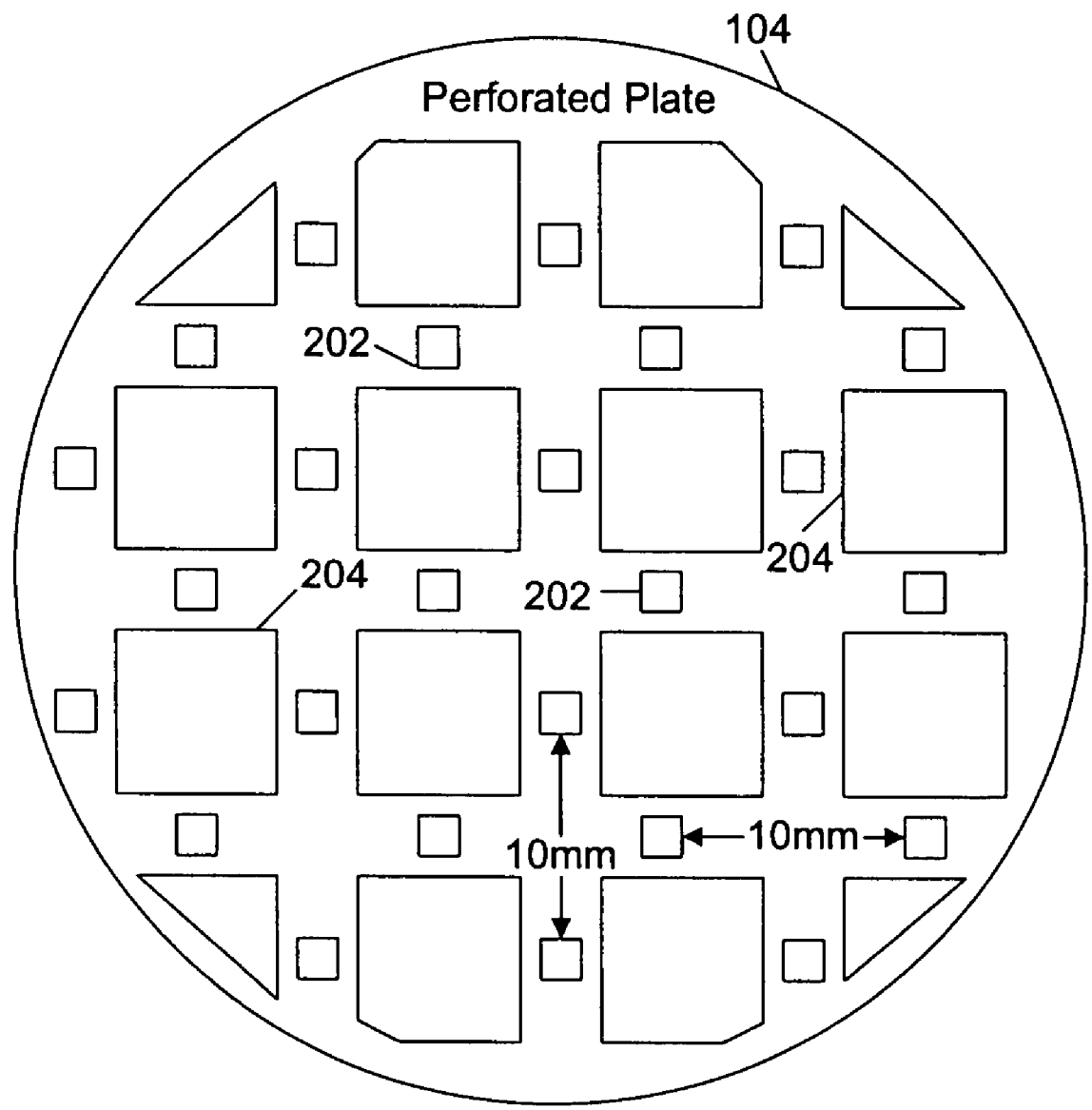
FIG. 2 is a front view of a perforated plate with UV light emitters mounted on its surface, in accordance with an embodiment of the invention.

FIG. 2 is a front view of a perforated plate 104 with UV light emitters 202 mounted on its surface, in accordance with an embodiment of the invention. Perforated plate 104 has UV light emitters 202 arranged in an array on its surface. Perforated plate 104 has perforations 204 to allow the fluid to pass through. In an embodiment of the invention, perforated plate 104 may be a Printed Circuit Board (PCB). In another embodiment of the invention, perforated plate 104 is a Metal Core Printed Circuit Board (MCPCB). The metal core of the MCPCB makes it a good conductor of heat. The metal core effectively transfers heat generated by UV light emitters 202 to a heat sink. Effective transfer of heat to the heat sink keeps UV light emitters 202 in their ideal operating temperature range, thereby increasing efficiency of system 100. Low temperatures are required for efficient operation of the LEDs, preferably in the range of 20° C. to 60° C.

In an embodiment of the invention, perforations 204 are square in shape. Perforations 204 allow the fluid to pass through and expose the micro-organisms present in the fluid to the UV light. Dimensions of perforations 204 determine proximity of the micro-organisms to UV light emitters 202. The dimensions of perforations 204 are decided based on UV light emission capacity of UV light emitters 202. The dimensions of perforations 204 are large for high power UV light emitters 202, whereas the dimensions of perforations 204 are small for low power UV light emitters 202.

In an embodiment of the invention, distance, hereinafter referred to as pitch, between two consecutive UV light emitters 202 is 10 millimeters (mm). A small pitch, 10 mm, of the UV light emitters 202 implies closer proximity of the micro-organisms to the UV light. The pitch of UV light emitters 202 depends on the UV light emission capacity of UV light emitters 202. The pitch is large for high power UV light emitters 202, and it is small for low power UV light emitters 202. A pitch of 10 mm ensures that at any point of time any micro-organism is not more than 5 mm away from UV light emitters 202. This ensures that a sufficient amount of the UV light is absorbed by the micro-organisms. High density of UV light emitters 202 on perforated plate 104 further increases exposure of the micro-organisms to the UV light.

In an embodiment of the invention, insulation windows are used to insulate UV light emitters 202 from the fluid. The insulation windows prevent short circuiting of electrical contacts by the fluid and protect the structure from contamination. The insulation windows facilitate transmission of the UV light to the fluid. In an embodiment of the invention, an insulation layer covers perforated plate 104. The insulation window and the insulation layer may be made from one of quartz, silicon dioxide, and glass.

Figure 3:
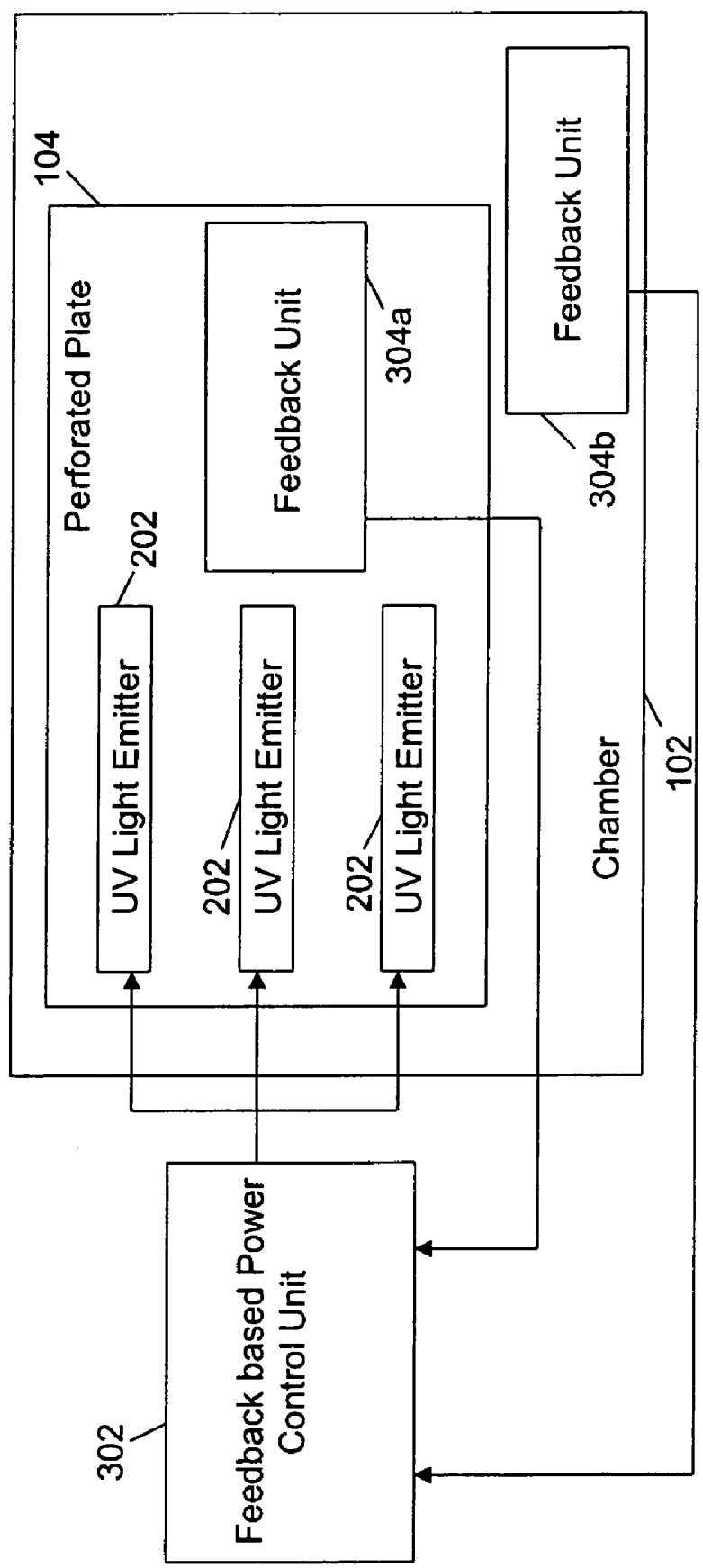
FIG. 3 is a block diagram illustrating interactions among a feedback-based power control unit, feedback units, and UV light emitters, in accordance with an embodiment of the invention.

FIG. 3 is a block diagram illustrating interactions among a feedback-based power control unit 302, feedback units 304a and 304b, and UV light emitters 202, in accordance with an embodiment of the invention. Feedback-based power control unit 302 is employed to control amount of power supplied to UV light emitters 202. Feedback based power control unit 302 takes input from feedback units 304a and 304b, and accordingly varies the amount of power supplied to UV light emitters 202. Feedback units 304a and 304b provide fluid-flow data and UV light intensity data to feedback based power control unit 302.

In an embodiment of the invention, feedback unit 304a is a fluid-flow sensor placed on perforated plate 104. Feedback unit 304a measures flow-rate inside chamber 102, and provides fluid-flow data to feedback-based power control unit 302. For example, when there is no flow of the fluid, feedback-based power control unit 302 switches off UV light emitters 202. As the fluid starts flowing, feedback unit 304a informs feedback-based power control unit 302 about the flow and feedback-based power control unit 302 switches on UV light emitters 202. Depending on flow-rate of the fluid, feedback-based power control unit 302 adjusts amount of power supplied to UV light emitters 202. If the flow-rate of the fluid increases, the time spent by the fluid inside chamber 102 decreases. This, in turn, decreases amount of the UV light absorbed by the micro-organisms. Therefore, as the flow-rate of the fluid increases, the intensity of the UV light generated by UV light emitters 202 is increased by supplying more power to UV light emitters 202. Similarly, if the flow-rate of the fluid decreases, the time spent by the fluid inside chamber 102 increases; and consequently, the micro-organisms absorb more than required amount of the UV light. Therefore, as the flow-rate decreases, the intensity of the UV light generated by UV light emitters 202 is decreased by supplying less power to UV light emitters 202, thereby saving electric power.

In an embodiment of the invention, feedback unit 304a accumulates information pertaining to the flow of the fluid by measuring change in temperature of perforated plate 104. The UV light emitters 202 heat up perforated plate 104. In the absence of any flow in the fluid, the temperature of perforated plate 104 remains constant. As the fluid starts flowing, the temperature of perforated plate 104 drops. Based on drop in the temperature of the fluid, feedback unit 304a measures the flow of the fluid and provides the fluid-flow data to feedback-based power control unit 302.

In another embodiment of the invention, feedback unit 304a calculates the fluid-flow data by measuring strain in perforated plate 104. The flow of the fluid develops different strains in different parts of perforated plate 104. Feedback unit 304a measures the strains and uses their values to calculate the fluid-flow data.

In an embodiment of the invention, feedback unit 304b is an UV light sensor inside chamber 102. Feedback unit 304b measures UV light intensity at its location and provides the UV light intensity data to feedback-based power control unit 302. The UV light output of UV light emitters 202 may vary over time. Feedback unit 304b, by measuring the UV light intensity, ensures that system 100 is working and meeting desired performance requirements. The UV light intensity is different in different parts of chamber 102 because turbidity of the fluid varies in different parts of chamber 102. Feedback unit 304b keeps a track of the turbidity of the fluid by measuring the UV light intensity inside chamber 102. Feedback-based power control unit 302 adjusts the power supplied to UV light emitters 202 based on the UV light intensity data provided by feedback unit 304b. Thereby, the intensity of UV light generated by UV light emitters 202 is adjusted according to the intensity of the UV light in different parts of chamber 102.

Figure 4:
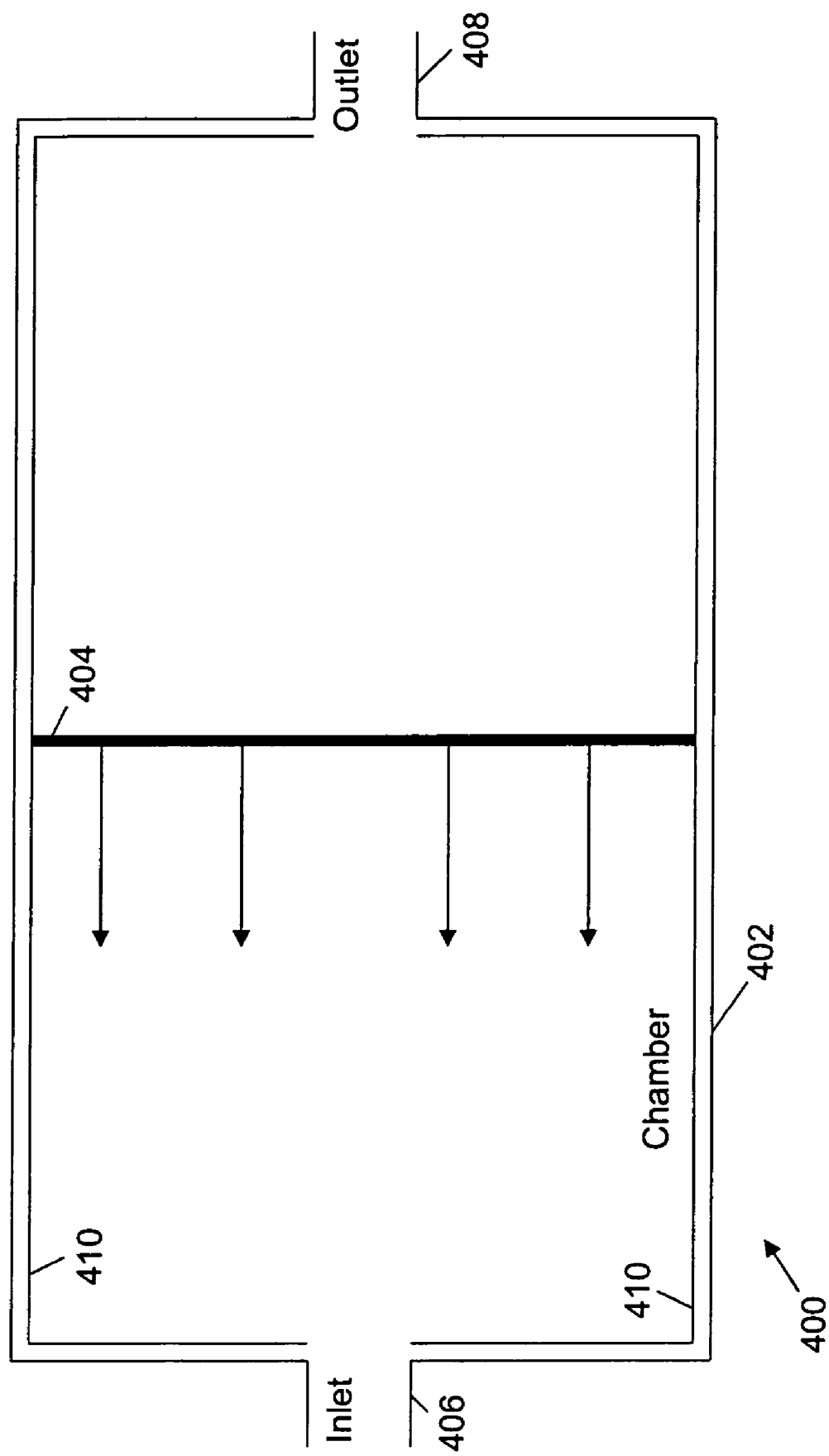
FIG. 4 is a diagram depicting a system with only one perforated plate for the purification of a fluid, in accordance with an embodiment of the invention.

FIG. 4 is a diagram depicting a system 400 with only one perforated plate for the purification of a fluid, in accordance with an embodiment of the invention. A chamber 402 houses a perforated plate 404 with UV light emitters mounted on it. Chamber 402 has an inlet 406 and an outlet 408. The fluid enters from inlet 406, passes through perforations on perforated plate 404, and comes out of chamber 402 from outlet 408. The UV light emitted by the UV light emitters mounted on perforated plate 404 disinfects micro-organisms present in the fluid. UV light-reflecting screens 410 reflect any UV light incident on them back to chamber 402.

Figure 5:
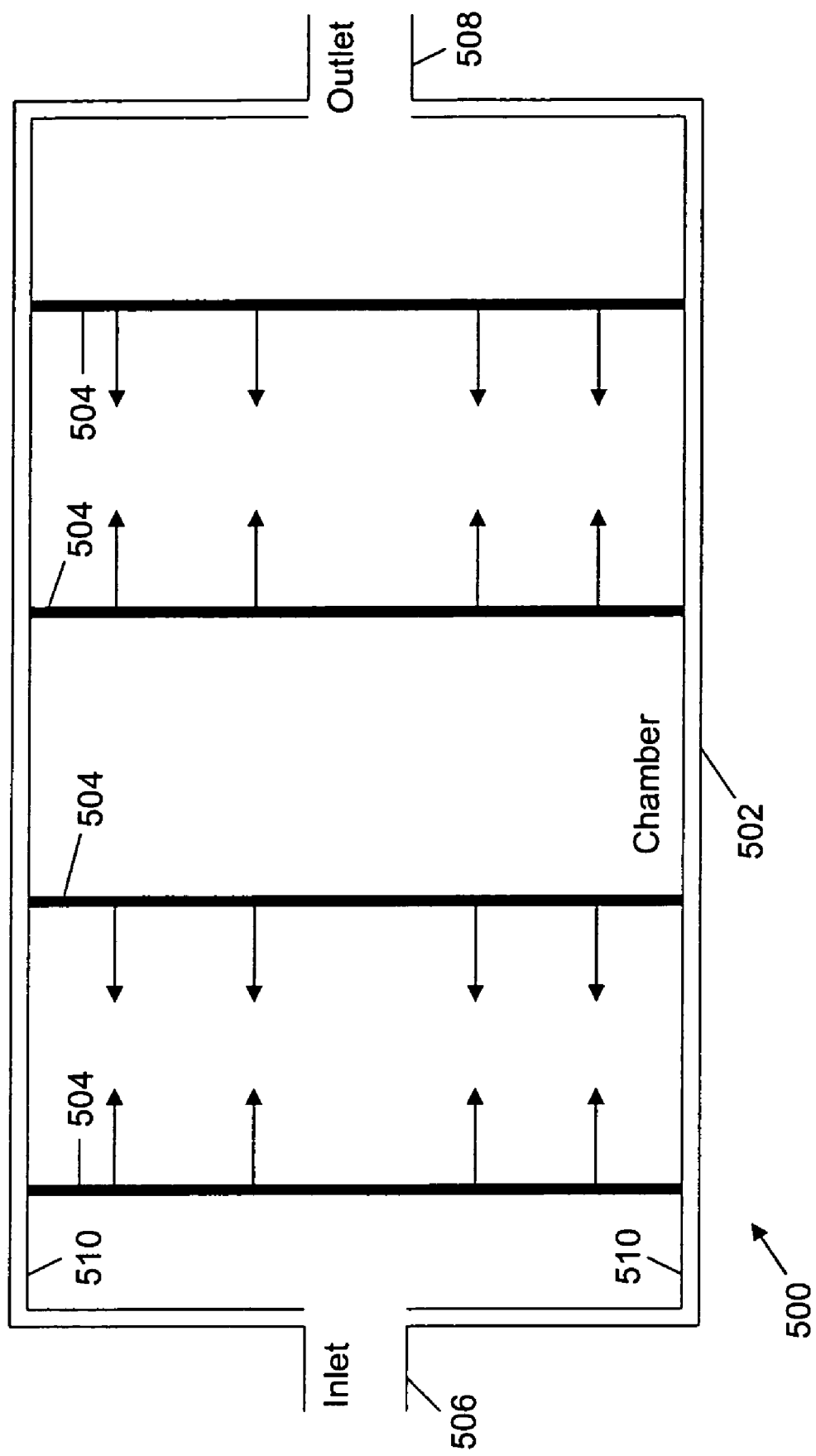
FIG. 5 is a diagram depicting a system with four perforated plates for the purification of a fluid, in accordance with an embodiment of the invention.

FIG. 5 is a diagram depicting a system 500 with four perforated plates for purification of a fluid, in accordance with an embodiment of the invention. A chamber 502 houses four perforated plates 504 with UV light emitters mounted on them. Chamber 502 has an inlet 506 and an outlet 508. The fluid enters from inlet 506, passes through perforations on perforated plates 504, and comes out of chamber 502 from outlet 508. The UV light emitted by the UV light emitters mounted on perforated plates 504 disinfects micro-organisms present in the fluid. UV light-reflecting screens 510 reflect any UV light incident on them back to chamber 502.

Advantages of this system used for purification of fluids using UV light emitters include:

Greater exposure of the micro-organisms to the UV light emitters as both front and rear of the micro-organisms are exposed uniformly to the UV light.

Efficient use of electric power is achieved by varying the power supplied to the UV light emitters, based on input supplied by the feedback units to the feedback-based power control unit.

Longer life of the UV LEDs used for emission of the UV light.

Use of the fluid to be purified as a cooling agent for the UV light emitters. The fluid keeps the UV light emitters in an ideal operating temperature range.

Efficient transmission of heat from the UV light emitters to a heat sink by the metal core of the MCPCB. The metal core keeps the UV light emitters in an ideal operating temperature range.

Availability of information about flow of the fluid inside the chamber.

Availability of information about the intensity of UV light inside the chamber.

While particular embodiments of the present invention have been shown and described, it will be obvious to those skilled in the art that changes and modifications may be made without departing from this invention in its broader aspects and, therefore, the appended claims are to encompass within their scope all such changes and modifications as fall within the true spirit and scope of this invention.

What is claimed is:

1. A system for purification of a fluid comprising:
   a perforated plate having a face and a plurality of openings in the face;
   a plurality of ultra violet (UV) light emitting diodes (LEDs) mounted on the face and distributed over the face so that at least one UV LED is between each set of adjacent openings in the face, such that fluid passing through each opening is irradiated by at least one UV LED located next to each opening to expose the fluid passing through each opening to UV radiation; and
   a chamber with at least one inlet and at least one outlet for the fluid, the perforated plate and UV LEDs being mounted in the chamber such that the fluid passes through the plurality of openings while being exposed to the UV radiation from the UV LEDs.

2. The system of claim 1, wherein the perforated plate comprises a printed circuit board.

3. The system of claim 1, wherein the openings and the UV LEDs are arranged in a two-dimensional array.

4. The system of claim 1 further comprising one or more insulation windows, said one or more insulation windows insulating said one or more UV LEDs from said fluid.

5. The system of claim 4, wherein said one or more insulation windows are made of a material selected from a group consisting of quartz, silicon dioxide, and glass.

6. The system of claim 1, wherein walls of said chamber are covered with one or more ultra violet light reflecting screens.

7. The system of claim 1 further comprising a feedback based power control unit, said feedback based power control unit supplying power to said one or more UV LEDs.

8. The system of claim 7 further comprising a feedback unit, said feedback unit providing information about physical conditions inside said chamber to said feedback based power control unit.

9. The system of claim 8, wherein said feedback unit comprises one or more ultra violet light sensors, said one or more ultra violet light sensors providing ultra violet light intensity data to said feedback based power control unit.

10. The system of claim 8, wherein said feedback unit comprises one or more fluid flow sensors, said one or more fluid flow sensors providing fluid flow data to said feedback based power control unit.

11. The system of claim 10, wherein said one or more fluid flow sensors measure temperature change of the perforated plate.

12. The system of claim 10, wherein said one or more fluid flow sensors measure strain in the perforated plate.

13. The system of claim 10, wherein said one or more fluid flow sensors are mounted on the perforated plate.

14. A system for purification of a fluid comprising:
    a perforated plate having a face and a plurality of openings in the face;
    a plurality of ultra violet (UV) light emitting diodes (LEDs) mounted on the face and distributed over the face so that at least one UV LED is between each set of adjacent openings in the face, such that fluid passing through each opening is irradiated by at least one UV LED located next to each opening to expose the fluid passing through each opening to UV radiation; and
    a feedback based power control unit, said feedback based power control unit supplying power to said one or more UV LEDs.

15. The system of claim 14 further comprising one or more insulation windows, said one or more insulation windows insulating said one or more UV LEDs from said fluid.

16. The system of claim 14 further comprising a feedback unit, said feedback unit for providing information to said feedback based power control unit about physical conditions inside a chamber housing the perforated plate.

* * * * *